US009994641B2

(12) United States Patent
Sonoda et al.

(10) Patent No.: US 9,994,641 B2
(45) Date of Patent: Jun. 12, 2018

(54) ANTI-HUMAN TRANSFERRIN RECEPTOR ANTIBODY THAT PASSES THROUGH BLOOD-BRAIN BARRIER

(71) Applicant: JCR Pharmaceuticals Co., Ltd., Hyogo (JP)

(72) Inventors: Hiroyuki Sonoda, Hyogo (JP); Hideto Morimoto, Hyogo (JP); Yuri Koshimura, Hyogo (JP); Masafumi Kinoshita, Hyogo (JP); Haruna Takagi, Hyogo (JP); Yoshiko Yoshii, Hyogo (JP)

(73) Assignee: JCR PHARMACEUTICALS CO., LTD., Hyogo (JP)

( * ) Notice: Subject to any disclaimer, the term of this patent is extended or adjusted under 35 U.S.C. 154(b) by 0 days. days.

(21) Appl. No.: 15/107,839

(22) PCT Filed: Dec. 24, 2014

(86) PCT No.: PCT/JP2014/084198
§ 371 (c)(1),
(2) Date: Jul. 29, 2016

(87) PCT Pub. No.: WO2015/098989
PCT Pub. Date: Jul. 2, 2015

(65) Prior Publication Data
US 2016/0369001 A1  Dec. 22, 2016

(30) Foreign Application Priority Data

Dec. 25, 2013  (JP) ................ P2013-266880

(51) Int. Cl.
*C07K 16/28* (2006.01)
*C12N 9/16* (2006.01)
*A61K 38/00* (2006.01)
*A61K 39/00* (2006.01)

(52) U.S. Cl.
CPC ............ *C07K 16/2881* (2013.01); *C12N 9/16* (2013.01); *C12Y 301/06013* (2013.01); *A61K 38/00* (2013.01); *A61K 2039/505* (2013.01); *C07K 2317/21* (2013.01); *C07K 2317/34* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| 5,154,924 A | 10/1992 | Friden et al. |
| 5,977,307 A | 11/1999 | Friden et al. |
| 8,992,913 B2* | 3/2015 | Mader .................... C07K 16/22 424/130.1 |
| 2004/0101904 A1 | 5/2004 | Pardridge et al. |
| 2006/0257412 A1* | 11/2006 | Bowdish ............ C07K 16/2851 424/178.1 |
| 2009/0123921 A1* | 5/2009 | Georgiou ............ C07K 14/245 435/6.16 |
| 2011/0110935 A1 | 5/2011 | Pardridge et al. |
| 2011/0245592 A1 | 10/2011 | Schoolcraft et al. |
| 2012/0328619 A1* | 12/2012 | Fey .................... C07K 16/2803 424/136.1 |

FOREIGN PATENT DOCUMENTS

| JP | H06-228199 A | 8/1994 |
| JP | 2006-511516 A | 4/2006 |
| JP | 2007-504166 A | 3/2007 |
| JP | 2009-525963 A | 7/2009 |
| JP | 2011-144178 A | 7/2011 |
| JP | 2012-29685 | 2/2012 |
| JP | 2012-062312 A | 3/2012 |
| JP | 2013-507131 A | 3/2013 |
| WO | 1991/04014 | 4/1991 |
| WO | 2009/072660 | 6/2009 |
| WO | 2011/044542 A1 | 4/2011 |
| WO | 2012/075037 | 6/2012 |
| WO | 2012/101998 | 8/2012 |
| WO | 2013/059617 | 4/2013 |

OTHER PUBLICATIONS

Parkkila et al. (PNAS, vol. 94, pp. 13198-13202, Nov. 1997).*
Chen 1995 "enhancement and destruction of antibody function by somatic mutation: unequal occurrence is controlled by v gene combinatorial associations" EMBO 14(12):2784-2794 (Year: 1995).*
International Search Report and Written Opinion, dated Apr. 7, 2015, International Patent Application No. PCT/JP2014/084198 with English translation (21 pages).
Li et al., "Genetically engineered brain drug delivery vectors: cloning, expression and in vivo application of an anti-transferrin receptor single chain antibody-streptavadin fusion gene and protein", Protein Engineering, 1999, vol. 12, No. 9, pp. 787-796.
Zewea et al., "Cloning and cytotoxicity of a human pancreatic RNase immunofusion", Immunotechnology, 1997, vol. 3, pp. 127-136.
Newton et al., "Angiogenin single-chain immunofusions: influence of peptide linkers and spacers between fusion protein domains", Biochemistry, 1996, vol. 35, pp. 545-553.
Zhou et al., "Brain-penetrating IgG-Iduronate 2-Sulfatase fusion protein for the mouse", Drug metabolism and Disposition, 2012, vol. 40, No. 2, pp. 329-335.
Zhou et al., "Selective plasma pharmacokinetics and brain uptake in the mouse of enzyme fusion proteins derived from species-specific receptor-targeted anti-bodies", Journal of Drug Targeting, 2012, vol. 20, No. 8, pp. 715-719.

(Continued)

*Primary Examiner* — Adam Weidner
(74) *Attorney, Agent, or Firm* — Hamre, Schumann, Mueller & Larson, P.C.

(57) ABSTRACT

Disclosed are a novel anti-human transferrin receptor antibody comprising an amino acid sequence selected from the group consisting of SEQ ID NOs: 4, 5, 6 and 7 that can pass through the blood-brain barrier, a fusion protein comprising a protein necessary to be brought into function in the central nervous system and the antibody, and method of their production. The fusion protein comprises amino acid sequences of an anti-human transferrin receptor antibody that recognizes an amino acid sequence selected from the group consisting of SEQ ID NOs:1, 2, and 3, and of other protein that is bound thereto on the C-terminal side.

10 Claims, 2 Drawing Sheets

(56) References Cited

OTHER PUBLICATIONS

Luo et al., Construction and expression of bi-functional proteins of single-chain Fv with effector domains, J. Biochem., 1996, vol. 120, pp. 229-232.

Xie et al., "Transport of nerve growth factor encapsulated into liposomes across the blood-brain barrier: in vitro and in vivo studies", Journal of Controlled Release 2005, vol. 105, pp. 106-119.

Ou et al., "High-Dose Enzyme Replacement Therapy in Murine Hurler Syndrome", Mol Get metab., Feb. 2014, vol. 111, No. 2, pp. 116-122.

Li et al., "The role of the transferrin-transferrin-receptor system in drug delivery and targeting", Trends in Phamacol Sciences, vol. 23, No. 5, May 2002, p. 206-2094 pages.

Helguera et al., "An Antibody Recognizing the Apical Domain of Human Transferrin Receptor 1 Efficiently Inhibits the Entry of All New World Hemorrhagic Fever Arenaviruses", Journal of Virology, Apr. 2012, vol. 86, No. 7, p. 1024-4028, 5 pages.

* cited by examiner

ANTI-HUMAN TRANSFERRIN RECEPTOR ANTIBODY THAT PASSES THROUGH BLOOD-BRAIN BARRIER

TECHNICAL FIELD

The present invention relates to transfer, through the blood-brain barrier, of a protein necessary to be brought into function in the central nervous system (CNS). More specifically, it relates to particular anti-transferrin receptor antibodies, a fusion protein consisting of one of those antibodies and a protein necessary to be brought into function in the central nervous system fused thereto, as well as to a method to deliver such a protein to the central nervous system to bring it into function there, by administering the protein, which is necessary to be brought into function in the central nervous system, in the form of a fusion protein with a particular anti-transferrin receptor antibody.

BACKGROUND ART

Unlike the capillaries in such tissues as muscles and the like, the capillaries that supply the blood to most of the brain tissues except some areas including the circumventricular organs (pineal gland, pituitary body, area postrema, etc.) differ in that their endothelial cells are connected by tight intercellular junctions. Thus, passive transfer of substances from the blood to the brain is restricted, and although there are some exceptions, substances generally are unlikely to move into the brain from the capillaries except such compounds as are lipid-soluble or of low molecular weight (less than 200-500 Dalton) and electrically neutral around the physiological pH. This system, which restricts exchanges of substances between the blood and the tissue fluid of the brain through the endothelial cells of capillaries in the brain, is called blood-brain barrier or BBB. The blood-brain barrier restricts exchanges of substances not only between the blood and the brain but also between the blood and the tissue fluid of the central nervous system including the brain and the spine.

Owing to the blood-brain barrier, most of the cells of central nervous system escapes the effect of fluctuating concentrations of hormones and lymphokines in the blood, and thus are able to maintain their biochemical homeostasis.

The blood-brain barrier, however, imposes a problem when it comes to develop a medical drug. For example, although nerve growth factor (NGF), which is thought to be acting on cholinergic neurons in the central nervous system and working to maintain the viability of the cells by preventing apoptotic cell death, was expected to become a therapeutic drug for dementia caused by Alzheimer's disease, it was concluded that nerve growth factor would not function as a therapeutic drug for Alzheimer's disease because it, being unable to pass through the blood-brain barrier due to its molecular weight of over 10 kD, could not reach the affected site within the brain. Further, whereas an enzyme replacement therapy is carried out by intravenous supplementation with recombinant α-L-iduronidase as a therapy of mucopolysaccharide storage disease type 1 (Hurler syndrome), an inherited disease caused by α-L-iduronidase deficiency, the therapy is not effective for abnormality in the central nervous system (CNS) which is notable in Hurler syndrome because the enzyme cannot pass through the blood-brain barrier.

Development of various methods has been tried to enable the passage, through the blood-brain barrier, of such macromolecular compounds as proteins or the like necessary to be brought into function in the central nervous system. In the case of nerve growth factor, for example, attempts have been made for a method to cause the factor to pass through the blood-brain barrier by preparing it in a liposome-encapsulated form and letting those liposomes fuse with the cell membrane of endothelial cells in brain capillaries, but the attempts have failed to make the method materialize (Non-patent Document 1). In the case of α-L-iduronidase, an attempt was made to enhance the passive transfer of the enzyme through the blood-brain barrier by raising its blood concentration through an increased single dose of the enzyme, and it was demonstrated, using a Hurler syndrome animal model, that the abnormality in the central nervous system was ameliorated by the method (Non-patent Document 2).

Furthermore, an attempt has also been made to administer a macromolecular compound directly in the spinal cavity or into the brain. For example, reports have been made about a method in which human α-L-iduronidase was administered into the spinal cavity of a patient with a Hurler syndrome (mucopolysaccharide storage disease type 1)(Patent Document 1), a method in which human acid sphingomyelinase was administered into the brain ventricles of a patient with Niemann-Pick disease (Patent Document 2), and a method in which iduronate 2-sulfatase (I2S) was administered into the brain ventricles of Hunter syndrome model animals (Patent Document 3). While it seems possible by one of such methods to definitely let a medical drug act in the central nervous system, they are highly invasive.

There have been reported various methods to let a macromolecular compound get to the brain through the blood brain barrier, in which the macromolecular compound is modified to give it an affinity to a membrane protein occurring on the endothelial cells of brain capillaries, thereby inducing formation of its complex with the membrane protein, so that it then passes through the blood-brain barrier by endocytosis. Examples of those membrane proteins occurring on the endothelial cells of the brain capillaries include insulin, transferrin, insulin-like growth factor (IGF-I, IGF-II) as well as receptors for LDL and leptin.

For example, a technique has been reported in which nerve growth factor (NFG) is synthesized into the form of a fusion protein with insulin, and with the help of its binding to the insulin receptor, this fusion protein is allowed to pass through the blood-brain barrier (Patent Documents 4-6). Further, a technique has been reported in which nerve growth factor (NGF) is synthesized in the form of a fusion protein with anti-insulin receptor antibody, and with the help of its binding to the insulin receptor, this fusion protein is allowed to pass through the blood brain barrier (Patent Documents 4 and 7). Further, a technique has been reported in which nerve growth factor (NGF) is synthesized in the form of a fusion protein with transferrin, and with the help of its biding to transferrin receptor (TfR), this fusion protein is allowed to pass through the blood brain barrier (Patent Document 8). Further, a technique has been reported in which nerve growth factor (NGF) is synthesized in the form of a fusion protein with anti-transferrin receptor antibody (anti-TfR antibody), and with the help of its binding to transferrin receptor, this fusion protein is allowed to pass through the blood brain barrier (Patent Documents 4 and 9).

Looking further into the techniques that utilize anti-transferrin receptor antibody, there has been reported in the field of a technique to make a drug pass through the blood-brain barrier by biding it to an anti-TfR antibody, that a single-chain antibody can be used consisting of the heavy chain of an anti-TfR antibody on whose C-terminal side is bound, through a linker, its light chain (Non-patent Document 3). Further, an anti-hTfR antibody exhibiting a dissociation constant of 30 nM to 1 μM with hTfR can be used profitably in a technique to make a drug pass through the blood-brain barrier (Patent Document 10). Furthermore, it has been reported that a lysosomal enzyme such as I2S can be allowed to pass through the blood-brain barrier by preparing it into a fusion protein in which it is bound to an anti-TfR antibody (Patent Document 11). There also are reports of techniques based on an anti-hTfR antibody and liposomes in combination, in which a drug is led to pass through the blood-brain barrier by preparing it into an encapsulated form in liposomes that carry the anti-hTfR antibody on their surface (Patent Documents 12 and 13).

To consider utilization, as medicine, of a fusion protein constructed with the above antibody, there is a possibility that a hyper reaction like an immune response to the antibody could take place after the administration of the fusion protein, thus making its further administration difficult. Therefore, to prepare for such an event, it would be highly meaningful to provide fusion proteins in advance that are constructed with some antibodies different from those currently employed, in order to avoid termination of treatment because of such a hyper reaction.

PRIOR ART DOCUMENTS

Patent Documents

Patent Document 1: JP2007-504166 A1
Patent Document 2: JP2009-525963 A1
Patent Document 3: JP2012-062312 A1
Patent Document 4: U.S. Pat. No. 5,154,924 B1
Patent Document 5: JP2011-144178 A1
Patent Document 6: US 2004/0101904 A1
Patent Document 7: JP2006-511516 A1
Patent Document 8: JPH06-228199 A1
Patent Document 9: JP5977307 B1
Patent Document 10: WO2012/075037
Patent Document 11: JP2013-507131 A1
Patent Document 12: WO1991/04014
Patent Document 13: WO2013/059617

Non-Patent Documents

Non-Patent Document 1: Xie Y. et al., J Control Release. 105. 106-19(2005)
Non-Patent Document 2: Ou L. et at, Mol Genet Metab. (2013)
Non-Patent Document 3: Li JY. Protein Engineering. 12. 787-96(1999)

SUMMARY OF INVENTION

Technical Problem

Against the above background, the objective of the present invention is to provide a novel anti-transferrin receptor antibody that can pass through the blood-brain barrier, and a fusion protein comprising a protein necessary to be brought into function in the central nervous system after administration into the blood and such an antibody, as well as a method for their production or use.

Solution to Problem

As a result of intense studies addressed to the above objective, the present inventors found a novel anti-human transferrin receptor antibody that can make lysosomal enzymes pass through the blood-brain barrier in a fused form with it, and thus completed the present invention. Consequently, the present invention provides what follows.

1. An anti-human transferrin receptor antibody that recognizes an amino acid sequence selected from the group consisting of SEQ ID NOs: 1, 2, and 3.

2. The anti-human transferrin receptor antibody according to 1 above that recognizes a partial sequence consisting of at least ten consecutive amino acid residues occurring in the amino acid sequence selected from the group consisting of SEQ ID NOs: 1, 2, and 3.

3. The anti-human transferrin receptor antibody according to 1 or 2 above, wherein the anti-human transferrin receptor antibody is a single-chain antibody comprising an amino acid sequence comprising the whole or part of the variable region of the light chain, an amino acid sequence that is bound thereto on the C-terminal side and consists of 15-25 amino acid residues as a first linker sequence, and further an amino acid sequence that is bound thereto on the C-terminal side and comprises the whole or part of the variable region of the heavy chain.

4. The anti-human transferrin receptor antibody according to 3 above comprising an amino acid sequence selected from the group consisting of SEQ ID NOs: 4, 5, 6 and 7.

5. A fusion protein comprising an anti-human transferrin receptor antibody according to one of 1 to 4 above and an amino acid sequence of other protein that is bound thereto on the C-terminal side.

6. A fusion protein comprising an anti-human transferrin receptor antibody according to one of 1 to 4 above and an amino acid sequence that is bound thereto on the C-terminal side and consists of 3-50 amino acid residues as a second linker sequence, and further an amino acid sequence of the said other protein that is bound thereto on the C-terminal side.

7. The fusion protein according 5 or 6 above, wherein the said other protein is a lysosomal enzyme.

8. The fusion protein according to 7 above, wherein the lysosomal enzyme is human iduronate 2-sulfatase 9. A DNA encoding an anti-human transferrin receptor antibody according to one of 1 to 4 above.

10. A DNA encoding the fusion protein according to one of 5 to 8 above.

11. A mammalian expression vector comprising the DNA according to 10 above incorporated therein.

12. A mammalian cell transformed with the mammalian expression vector according to 11 above.

13. The cell according to 12 above, wherein the mammalian cell is a CHO cell.

Effects of Invention

The present invention enables provision of proteins that are intended to be brought into function in the central nervous system (CNS), in particular, physiologically active proteins, in the form that allow them to pass through the blood-brain barrier, by preparing them as a fusion proteins with an anti-human transferrin receptor antibody, thus making it possible that such physiologically active proteins function directly in the brain after their administration into the blood.

DESCRIPTION OF EMBODIMENTS

Figure 1A:
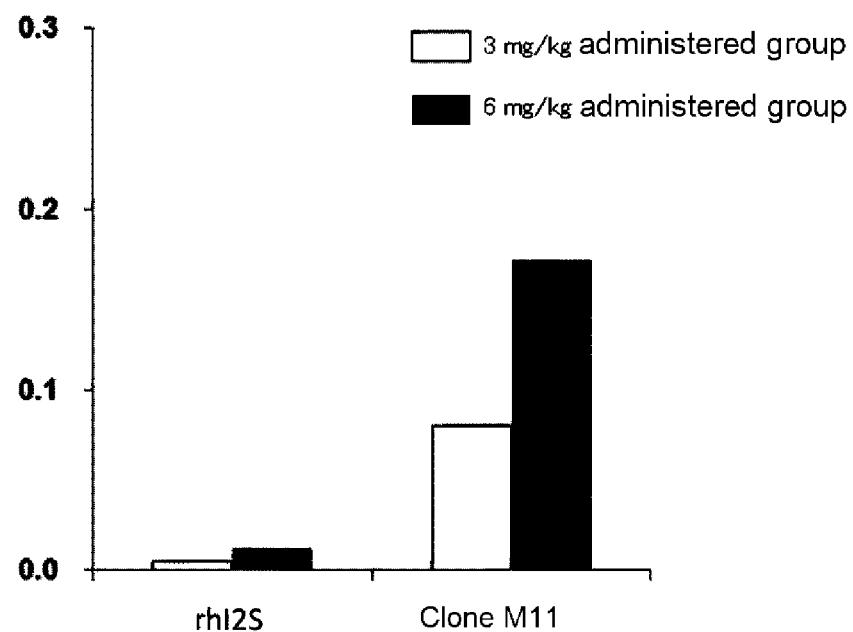
FIG. 1A illustrates the result of brain distribution test of hI2S-sc-anti-hTfR antibody fusion protein produced by transformed *E. coli* Cone M11, after it was injected into the tail vein of a mouse, along with the result with rhI2S. The vertical axis indicates the I2S concentration in brain homogenate (μg/wet weight)(mean of two animals per group).

In the present invention, the term a "single-chain antibody" refers to an antibody that has a sequence comprising the whole or part of the variable region of the light chain of an immunoglobulin, a first linker sequence on the C-terminus, and further an amino acid sequence comprising the whole or part of the heavy chain of the immunoglobulin on the C-terminal side, and that specifically binds to a particular antigen. The variable region of the light chain of an immunoglobulin has three complementarity determining regions (CDRs), which directly contact the antigen and determine the antibody's specificity. In the same fashion, the variable region of the heavy chain of an immunoglobulin also has three CDRs. The CDRs are the regions that directly contact the antigen and determine the antibody's specificity. Therefore, it is preferred that a single-chain antibody has all the three CDRs of the heavy chain of an immunoglobulin together with all the three CDRs of the light chain of the immunoglobulin.

However, so long as the affinity of a single-chain antibody to its antigen is not severely impaired, a mutation, such as substitution, insertion, or deletion of one or more amino acids, may be introduced into the amino acid sequence of a CDR, and it is also possible to adjust as desired the affinity of the single-chain antibody to its antigen by introduction of a mutation. For example, in the case where a single-chain antibody has a high affinity to its antigen, making the dissociation constant in water excessively low, the single-chain antibody might not dissociate itself from the antigen after administered to the body, thus resulting in disadvantage for its functioning. In such a case, it is possible to stepwise adjust the dissociation constant to, e.g., 2 to 5 folds, 5 to 10 folds, 10 to 100 folds, of the original antibody, by introducing a mutation into the CDRs until a single-chain antibody most fit the purpose is obtained. On the contrary, it is also possible to stepwise adjust the dissociation constant to, e.g., 1/2 to 1/5 fold, 1/5 to 1/10 fold, 1/10 to 1/100 fold of the original antibody. Such adjustment of the dissociation constant can be made by introducing the gene encoding a single-chain antibody into a phagemid, with which preparing a phage that expresses the single-chain antibody on the surface of the capsid, letting the phage multiply while introducing mutations into the gene encoding the single-chain antibody by application of mutagens and the like, and purifying the phage thus multiplied using an antigen column under a certain condition to obtain a single-chain antibody that exhibits a desirable dissociation constant.

In the present invention, the phrase "affinity of a single-chain antibody to its antigen" refers to the property of a single-chain antibody to specifically recognize and bind to the antigen, and the clause "a single-chain antibody has affinity to its antigen" means that a single-chain antibody specifically binds to its antigen at a dissociation constant of preferably 0.1 nM to 5 μM, and more preferably 1 nM to 1 μM, under a physiological condition.

The gene encoding a single-chain antibody can be constructed by synthesizing cDNA using as a template mRNAs extracted from spleen cells or peripheral blood mononuclear cells of an animal immunized with the antigen, or from spleen cells or peripheral blood cells immunized in vitro with the antigen, performing PCR using this cDNAs as a template to multiply both DNA fragments encoding the light chain of the immunoglobulin and DNA fragments encoding the heavy chain of the immunoglobulin, respectively, and then by multiplying them so that the DNA fragment encoding the light chain of the immunoglobulin is linked, on the 3'-end side thereof and via a DNA sequence encoding a first linker sequence, to the DNA fragment encoding the heavy chain of the immunoglobulin. On the contrary, it is also possible to multiply them so that the DNA fragment encoding the heavy chain of the immunoglobulin is linked on the 3'-end side thereof, via a DNA sequence encoding a first linker sequence, to the DNA fragment encoding the light chain of the immunoglobulin to construct the gene encoding a single-chain antibody. The gene that encodes a single-chain antibody constructed in such a manner is then joined by a start codon on the 5' end thereof so that the gene can express itself in animal cells. In the above, the DNA sequence encoding the first linker that is placed between the cDNAs of the light chain and heavy chain of the immunoglobulin is preferably those which encode the first linker consisting of preferably 15-25, more preferably 15-20, still more preferably 15 amino acid residues. While there is no specific limitation as to the amino acid sequence of such a first linker insofar as it allow the light and heavy chains of the immunoglobulin to take a configuration for recognition of the antigen, it preferably consists of glycine and serine, and has, for example, the amino acid sequence of SEQ ID NO: 8 (Gly Gly Gly Gly Ser Gly Gly Gly Gly Ser Gly Gly Gly Gly Ser).

In the present invention, the terms "single-chain anti-human transferrin receptor antibody", "single-chain anti-hTfR antibody", or "sc-anti-hTfR antibody" refer, among the above-mentioned single-chain antibodies, to those antibodies which specifically bind to human transferrin receptor as the antigen. The genes that encode such single-chain anti-hTfR antibodies can be prepared, in accordance with the above-mentioned procedure for production of the gene encoding a single-chain antibody, from the cDNAs synthesized using mRNAs extracted from spleen cells or peripheral blood mononuclear cells immunized in vitro with hTfR or with a peptide chain consisting of 13 to 25 amino acids of partial amino acid sequence of the peptide chain forming hTfR, as the antigen, or from the cDNA synthesized using mRNAs extracted from spleen cells or peripheral blood mononuclear cells obtained from animals immunized with such a peptide chain as the antigen. While there is no particular limitation as to the peptide chain forming the hTfR employed here so long as it can give an anti-hTfR antibody that specifically binds to hTfR under a physiological condition, the peptide chains having the following amino acid sequence can be preferably used:

(1)
(SEQ ID NO: 1)
Gly Lys Leu Val His Ala Asn Phe Gly Thr Lys Lys Asp Phe Glu (2)
(SEQ ID NO: 2)
Ser Ser Gly Leu Pro Asn Ile Pro Val Gln Thr Ile Ser Arg Ala Ala Ala Glu Lys Leu Phe Gly,
and (3)
(SEQ ID NO: 3)
Val Gly Ala Thr Glu Trp Leu Glu Gly Tyr Leu Ser Ser.

Thus, preferable embodiments of the single-chain anti-human transferrin receptor antibody of the present invention are those which recognize and specifically bind to one of the amino acid sequences presented as SEQ ID NOs: 1 to 3, each of which forms part of the peptide chain forming the human transferrin receptor, more preferably those which recognize an amino acid sequence consisting of at least 10 consecutive amino acid residues within the amino acid sequences presented as SEQ ID NOs: 1 to 3, and still more preferably those which recognize an amino acid sequence consisting of at least 13 consecutive amino acid residues within the amino acid sequences presented as SEQ ID NOs: 1 to 3.

As the gene encoding a single-chain anti-hTfR antibody produced according to the above method is obtained as a group of multiplication products by PCR from immunoglobulin genes having diverse DNA sequences, the gene encoding the single-chain anti-hTfR antibody of interest must be isolated from them. Thus, in order to screen the gene encoding the single-chain anti-hTfR antibody having desired properties, the genes encoding the single-chain anti-hTfR antibodies produced through the PCR multiplication must once be introduced into an expression vector for eukaryotic cells, such as mammalian cells, yeast cells or the like, or prokaryotic cells such as E. coli or the like, to produce a cDNA library of single-chain anti-hTfR antibodies. Using such an library, then, host cells are transformed to make them express one of those single-chain anti-hTfR antibodies, each of thus expressed single-chain anti-hTfR antibodies is measured for the affinity to its antigen, and thus the host cells that express the single-chain anti-hTfR antibody that has the desired affinity can thus be isolated and identified. Although the affinity of a single-chain anti-hTfR antibody with hTfR is preferably such that the dissociation constant is 1 nM to 1 μM under a physiological condition, this is not requisite but the affinity may be adjusted in accordance with the use of the single-chain anti-hTfR antibody.

In the present invention, the term "Sc-anti-hTfR antibody fusion protein" refers to a fusion protein consisting of a single-chain anti-hTfR antibody mentioned above to which is bound, on the C-terminal side, some other desired protein, directly or indirectly via a second linker sequence. Such an Sc-anti-hTfR antibody fusion protein can be obtained by providing a DNA fragment prepared by linking to the cDNA encoding the said other protein on the 5'-end side, a cDNA encoding a desired single-chain anti-hTfR antibody having affinity to hTfR, directly or indirectly via a DNA fragment encoding a linker sequence, then introducing this DNA fragment into an expression vector for eukaryotic organisms like mammalian cells or yeast, or for prokaryotic cells such as *E. coli*, and letting the vector express itself in those cells. In the above, the second linker sequence placed between the single-chain anti-hTfR antibody and the said other protein is a peptide chain consisting of preferably 3-50, more preferably 13-17, still more preferably 15 amino acids. Although there is no particular limitation as to the amino acid sequence of such a second linker sequence insofar as the single-chain anti-hTfR antibody to which is linked the linker sequence retains its affinity to hTfR and, simultaneously, the said other protein to which is linked the linker sequence can exhibit its physiological activity under a physiological condition, it is made up of glycine and serine, and has, for example, the amino acid sequence of SEQ ID NO:9 (Gly Gly Gly Gly Ser Gly Gly Gly Gly Ser Gly Gly Gly Gly Ser).

When administered to a human body, the Sc-anti-hTfR antibody fusion protein binds to hTfR expressed on the endothelial cells of the brain capillaries and passes through the blood-brain barrier into the brain with the help of the mechanism of endocytosis. Therefore, when administered to a human through the blood, an Sc-anti-hTfR antibody fusion protein that is formed by fusing a protein necessary to be brought into function in the brain with an Sc-anti-hTfR antibody can get into the brain and exhibit its function there, even if the protein by itself is otherwise unable to pass through the blood-brain barrier and thus not expected to function in the brain. Thus, by choosing a protein to be fused to an Sc-anti-hTfR antibody as desired, the resulting Sc-anti-hTfR antibody fusion protein can be used as an agent for treatment of Alzheimer's disease, Parkinson's disease, Huntington's disease, amyotrophic lateral sclerosis, brain tumors, lysosomal storage disease accompanied by encephalopathy, and diabetes mellitus, or the like. For example, nerve growth factor fused to an Sc-anti-hTfR antibody (NFG-Sc-anti-hTfR antibody) can be used as a drug for the treatment of dementia in Alzheimer's disease, α-L-iduronidase fused to an Sc-anti-hTfR antibody as a drug for the treatment of encephalopathy in Hurler syndrome, and iduronate 2-sulfatase fused to an Sc-anti-hTfR antibody as a drug for the treatment of encephalopathy in Hunter syndrome.

Examples of proteins that can exhibit their pharmacological effect when fused to an Sc-anti-hTfR antibody further include brain-derived neurotrophic factor (BDNF), ciliary neurotrophic factor (CNTF), glial cell line-derived neurotrophic factor (GDNF), various neurotrophins, activin, basic fibroblast growth factor (bFGF), epidermal growth factor (EGF), various cytokines, interferon α, interferon β, interferon γ, interleukin 6, granulocyte-macrophage colony stimulating factor (GM-CSF), granulocyte colony stimulating factor (G-CSF), macrophage colony stimulating factor (M-CSF), PD-1, and the like.

EXAMPLES

Although the present invention is described in further detail below with reference to examples, it is not intended that the present invention be limited to those examples.

[Preparation of Mouse Single-Chain Anti-hTfR Antibody cDNA Library]

Cells obtained from mouse spleen were divided and immunized by in vitro immunization with each of three respective peptides having part of the amino acid sequence of the peptide chain that forms human transferrin receptor (hTfR), i.e., Peptide 1 (shown as SEQ ID NO: 1), Peptide 2

(shown as SEQ ID NO: 2), Peptide 3 (shown as SEQ ID NO: 3), and with combined peptides of them, respectively. The in vitro immunization was carried out in accordance with the following general procedures. To a 15-mL centrifuge tube were added 1 nmol of a peptide chosen from the above, 5 μL of 10 mg/mL n-acetylmuramyl-L-alanyl-D-isoglutamine as adjuvant, and then 1.5×10⁷ cells obtained from the mouse spleen, and the tube was left undisturbed for 15 minutes at room temperature. Then, IL-4, IL-13, anti-CD40 antibody and LPS were added to the final concentration of 10 ng/mL, 10 ng/mL, 1 μg/mL, and 40 μg/mL, respectively, and following further addition of 3.5 mL of 40% FBS-containing RPMI1640 medium, culture was performed, in the presence of 5% $CO_2$, at 37° C. for two days. IL-21 was further added to the final concentration of 10 ng/mL, and culture was continued for further three days under the same conditions.

The total mRNAs were extracted from the immunized cells, and using them as a template, single-chain cDNAs were synthesized. On those single-chain cDNAs, the light chains and heavy chains of the immunoglobulin, respectively, were multiplied by PCR. To multiply the light chains of the immunoglobulin, the forward primers having one of the following nucleotide sequences presented as SEQ ID NOs: 10-27:

(1) VL-FW1:
(SEQ ID NO: 10)
ttcatggcggactacaaagayatccagctgactcagcc (2) VL-FW2:
(SEQ ID NO: 11)
ttcatggcggactacaaagayattgttctcwcccagtc (3) VL-FW3:
(SEQ ID NO: 12)
ttcatggcggactacaaagayattgtgmtmactcagtc (4) VL-FW4:
(SEQ ID NO: 13)
ttcatggcggactacaaagayattgtgytracacagtc (5) VL-FW5:
(SEQ ID NO: 14)
ttcatggcggactacaaagayattgtratgacmcagtc (6) VL-FW6:
(SEQ ID NO: 15)
ttcatggcggactacaaagayattmagatramccagtc (7) VL-FW7:
(SEQ ID NO: 16)
ttcatggcggactacaaagayattcagatgaydcagtc (8) VL-FW8:
(SEQ ID NO: 17)
ttcatggcggactacaaagayatycagatgacacagac (9) VL-FW9:
(SEQ ID NO: 18)
ttcatggcggactacaaagayattgttctcawccagtc

(10) VL-FW10:
(SEQ ID NO: 19)
ttcatggcggactacaaagayattgwgctsacccaatc

(11) VL-FW11:
(SEQ ID NO: 20)
ttcatggcggactacaaagayattstratgacccartc

(12) VL-FW12:
(SEQ ID NO: 21)
ttcatggcggactacaaagayrttktgatgacccarac

(13) VL-FW13:
(SEQ ID NO: 22)
ttcatggcggactacaaagayattgtgatgacbcagkc

(14) VL-FW14:
(SEQ ID NO: 23)
ttcatggcggactacaaagayattgtgataacycagga

(15) VL-FW15:
(SEQ ID NO: 24)
ttcatggcggactacaaagayattgtgatgacccagwt

(16) VL-FW16:
(SEQ ID NO: 25)
ttcatggcggactacaaagayattgtgatgacacaacc

(17) VL-FW17:
(SEQ ID NO: 26)
ttcatggcggactacaaagayattttgctgactcagtc

(18) VL-FW18:
(SEQ ID NO: 27)
ttcatggcggactacaaagatgctgttgtactcaggaatc and reverse primers having one of the following nucleotide sequences presented as SEQ ID NOs: 28-32:

(19) VL-RV1:
(SEQ ID NO: 28)
ggagccgccgccgccagaaccaccaccaccagaaccaccaccaccacgtt
tgatttccagcttgg

(20) VL-RV2:
(SEQ ID NO: 29)
ggagccgccgccgccagaaccaccaccaccagaaccaccaccaccacgtt
ttatttccagcttgg

(21) VL-RV3:
(SEQ ID NO: 30)
ggagccgccgccgccagaaccaccaccaccagaaccaccaccaccacgtt
ttatttccaactttg

(22) VL-RV4:
(SEQ ID NO: 31)
ggagccgccgccgccagaaccaccaccaccagaaccaccaccaccacgtt
tcagctccagcttgg

(23) VL-RV5:
(SEQ ID NO: 32)
ggagccgccgccgccagaaccaccaccaccagaaccaccaccaccaccta
ggacagtcagtttgg were employed.

Besides, in nucleotide sequences, "r" refers to "g" or "a"; "y" to "t" or "c"; "m" to "a" or "c"; "k" to "g" or "t"; "s" to "g" or "c"; "w" to "a" or "t"; "b" to "g", "c" or "t"; "d" to "a", "g" or "t"; and "v" to "a", "g" or "c", respectively.

Further, to multiply the heavy chains of the immunoglobulin, the forward primers having the following nucleotide sequence presented as SEQ ID NOs: 33-51:

(1) VH-FW1:
(SEQ ID NO: 33)
ggcggcggcggctccggtggtggtggatccgakgtrmagcttcaggagtc (2) VH-FW2:
(SEQ ID NO: 34)
ggcggcggcggctccggtggtggtggatccgaggtbcagctbcagcagtc (3) VH-FW3:
(SEQ ID NO: 35)
ggcggcggcggctccggtggtggtggatcccaggtgcagctgaagsastc (4) VH-FW4:
(SEQ ID NO: 36)
ggcggcggcggctccggtggtggtggatccgaggtccarctgcaacartc -continued (5) VH-FW5:
(SEQ ID NO: 37)
ggcggcggcggctccggtggtggtggatcccaggtycagctbcagcartc (6) VH-FW6:
(SEQ ID NO: 38)
ggcggcggcggctccggtggtggtggatcccaggtycarctgcagcagtc (7) VH-FW7:
(SEQ ID NO: 39)
ggcggcggcggctccggtggtggtggatcccaggtccacgtgaagcagtc (8) VH-FW8:
(SEQ ID NO: 40)
ggcggcggcggctccggtggtggtggatccgaggtgaasstggtggaatc (9) VH-FW9:
(SEQ ID NO: 41)
ggcggcggcggctccggtggtggtggatccgavgtgawgytggtggagtc

(10) VH-FW10:
(SEQ ID NO: 42)
ggcggcggcggctccggtggtggtggatccgaggtgcagskggtggagtc

(11) VH-FW11:
(SEQ ID NO: 43)
ggcggcggcggctccggtggtggtggatccgakgtgcamctggtggagtc

(12) VH-FW12:
(SEQ ID NO: 44)
ggcggcggcggctccggtggtggtggatccgaggtgaagctgatggartc

(13) VH-FW13:
(SEQ ID NO: 45)
ggcggcggcggctccggtggtggtggatccgaggtgcarcttgttgagtc

(14) VH-FW14:
(SEQ ID NO: 46)
ggcggcggcggctccggtggtggtggatccgargtraagcttctcgagtc

(15) VH-FW15:
(SEQ ID NO: 47)
ggcggcggcggctccggtggtggtggatccgaagtgaarsttgaggagtc

(16) VH-FW16:
(SEQ ID NO: 48)
ggcggcggcggctccggtggtggtggatcccaggttactctraaagwgtstg

(17) VH-FW17:
(SEQ ID NO: 49)
ggcggcggcggctccggtggtggtggatcccaggtccaactvcagcarcc

(18) VH-FW18:
(SEQ ID NO: 50)
ggcggcggcggctccggtggtggtggatccgatgtgaacttggaagtgtc

(19) VH-FW19:
(SEQ ID NO: 51)
ggcggcggcggctccggtggtggtggatccgaggtgaaggtcatcgagtc and reverse primers having the following nucleotide sequence presented as SEQ ID NOs: 52-55:

(20) VH-RV1:
(SEQ ID NO: 52)
ggcaagctttacctgcagcgaggaaacggtgaccgtggt

(21) VH-RV2:
(SEQ ID NO: 53)
ggcaagctttacctgcagcgaggagactgtgagagtggt

(22) VH-RV3:
(SEQ ID NO: 54)
ggcaagctttacctgcagcgcagagacagtgaccagagt

-continued

(23) VH-RV4:
(SEQ ID NO: 55)
ggcaagctttacctgcagcgaggagacggtgactgaggt were employed.

Then, an equal molar amount of the cDNA for the light chain and the cDNA for the heavy chain of the immunoglobulin respectively obtained above through their multiplication by PCR were mixed and subjected to PCR to multiply the cDNA encoding a single-chain anti-hTfR antibody consisting of the cDNA for the light chain and the cDNA for the heavy chain linked on the 3' side thereof via a nucleotide sequence encoding a peptide chain having the amino acid sequence presented as SEQ ID NO:9 as a first linker sequence. Then, using this cDNA encoding the single-chain anti-hTfR antibody obtained through multiplication as a template, PCR was performed with a forward primer having a nucleotide sequence (ggcgaattcatggcggactacaaag) presented as SEQ ID NO:56 and a reverse primer having a nucleotide sequence (ggcaagctttactgcagcg) presented as SEQ ID NO:57. The multiplication product thus obtained was cut with EcoRI/HindIII and inserted the EcoRI/HindIII site site site site of a *E. coli* expression plasmid pMAL-c2E (New England Biolabs) so that a maltose binding protein will fuse on the N-terminal side of the of the of the of the of the of the peptide chain encoded by the multiplication product. The product thus obtained was designated mouse was designated mouse single-chain anti-hTfR antibody cDNA library. Preparation of this cDNA library was performed in accordance with the method described in WO 2009/072660 and JP2012-29685 A1.

[Preparation of Human Single-Chain Anti-hTfR Antibody cDNA Library]

In the same manner as described above for the preparation of mouse single-chain anti-hTfR antibody cDNA library, human peripheral blood mononuclear cells (Lonza) were immunized using in vitro immunization with Peptide 1 (shown as SEQ ID NO: 1), Peptide 2 (shown as SEQ ID NO: 2), Peptide 3 (shown as SEQ ID NO: 3), and with combined peptides of them, respectively, and the total mRNAs were extracted, which then was used as a template to prepare a human single-chain anti-hTfR antibody cDNA library.

[Screening of Single-Chain Anti-hTfR Antibody cDNA Library]

*E. coli* (JM109) was transformed respectively with the mouse and human single-chain anti-hTfR antibody cDNA libraries, and then disseminated on LB plates containing ampicillin (Amp), and cultured overnight at 37° C. On the following day, the colonies formed on the plates were collected one by one, with which Overnight Express™ Instant LB Medium (Novagen), which had been dispensed beforehand to 96-well plates, was inoculated. After the plates were shaken overnight at 37° C., a tenth amount of Popculture Reagent (Novagen) was added to lyse the cells, and following addition of an equal amount of TBS-T, the resulting mixture was centrifuged to collect the supernatant. This supernatant was used as a sample solution.

To each well of the 96-well plates was added 5 μg/mL of recombinant human TfR (rhTfR) (Sino Biological) or 50 μL of bovine gamma globulin (Bio-Rad, Inc.), and the plates were left undisturbed at 4° C. overnight. After removal of the solution, each well was washed once with 300 μL of TBS-T. Then, to each well was added 300 μL of 1% BSA solution, and the plates were left undisturbed for 30 minutes at room temperature. After removal of the solution, 100 μL of the above sample solution was added to each well, and the plates were left undisturbed for two hours at room temperature. After removal of the solution, each well was washed three times with 300 μL of TBS-T, and 50 μL of HRP-labelled anti MBP antibody (Novagen) was added, and the plates were left undisturbed for one hour at room temperature. After removal of the solution, each well was washed three times with 300 μL of TBS-T, then 50 μL of POD substrate solution (Nacalai Tesque, Inc.) was added, and a reaction was allowed to proceed for 10-15 minutes at room temperature. The reaction was terminated by addition of 100 μL of 0.2N HCl solution, absorbance at 450 nm was measured on a plate reader to identify those clones which expressed a single-chain anti-rhTfR antibody exhibiting a high affinity to rhTfR (high affinity clones to rhTfR). Three clones, M11, M23 and M27 were obtained as high affinity clones to rhTfR from the mouse single-chain anti-hTfR antibody cDNA library. A clone (B84) was obtained as a high affinity clone to rhTfR from the human single-chain anti-hTfR antibody cDNA library.

In the above, Clone M11 was obtained by screening the single-chain anti-hTfR antibody library derived from the cells immunized with Peptide 2 (SEQ ID NO: 2) and Peptide 3 (SEQ ID NO: 3); Clone M23 with Peptide 2 (SEQ ID NO: 2) and Peptide 3 (SEQ ID NO: 3); Clone M27 with Peptide 2 (SEQ ID NO: 2) and Peptide 3 (SEQ ID NO: 3); and Clone B84 with Peptide 1 (SEQ ID NO: 1), respectively. Therefore, Clone M11, Clone M23, Clone M27 were clones expressing a mouse single-chain anti-hTfR antibody that recognizes the whole or part of the amino acid sequence of Peptide 2 or Peptide 3 as the epitope, and Clone B84 is a clone expressing human single-chain anti-hTfR antibody that recognizes the whole or part of the amino acid sequence of Peptide 1.

[Analysis of High Affinity Clones to rhTfR]

Expression vectors were purified from the four high affinity clones to rhTfR obtained by the above screening, and the amino acid sequence of the single-chain anti-rhTfR antibody encoded by each of the clones was analyzed. As a result, it was found that Clone M11 encoded the single-chain anti-rhTfR antibody having the amino acid sequence presented as SEQ ID NO: 4, Clone M23 as SEQ ID NO: 5, Clone 27 as SEQ ID NO: 6, and Clone B84 as SEQ ID NO: 7, respectively.

[Preparation of a Fusion Protein of Human Iduronate-2-Sulfatase and a Single-Chain Anti-rhTfR Antibody]

Expression vectors were purified from the above four high affinity clones to rhTfR, which then was digested with EcoRI/HindIII and subjected to agarose gel EcoRI/HindIII electrophoresis, and a DNA fragment consisting of approximately 700 bp was cut out that encoded a single-chain anti-rhTfR antibody, and this DNA fragment was inserted into the EcoRI/HindIII site of pET32a vector. *E. coli* (JP109) was transformed with the vector thus obtained, disseminated on LB plates containing ampicillin (Amp), and cultured overnight at 37° C. On the following day, the colonies formed on the plates were cultured in LB medium, and vectors then were collected for each clone.

The vectors collected was digested with BglII/NotI and subjected to agarose gel electrophoresis, and a DNA fragment consisting of approximately 700 bp was cut out that encoded a single-chain anti-rhTfR antibody. Using a human placenta cDNA library (Takara Bio) as a template, nested PCR was performed with two primer sets, i.e., the outer primer set used in the first reaction:

(a) I2S-f:
(SEQ ID NO: 58)
ACGCCTATTGCTGCAGGATG,
and (b) I2S-r:
(SEQ ID NO: 59)
AAACGACCAGCTCTAACTCC, and the inner primer set used in the second reaction:

(c) I2S-f2:
(SEQ ID NO: 60)
ATActcgagGCCACCATGCCGCCACCCCGG,
and (d) I2S-r2:
(SEQ ID NO: 61)
TTCTTATgcggccgcTCAAGGCATCAACAA, to multiply a DNA fragment containing the cDNA encoding human iduronate-2-sulfatase (hI2S). This multiplication product was digested with XhoI and NotI, and inserted into the XhoI and NotI site of mammalian expression vector pE-neo7 to give pE-neo-I2S. In the above, pE-neo7 was prepared in accordance with the method described in WO 2012/101998.

PE-neo-hI2S was digested with BglII/NotI, into which was inserted the DNA fragment consisting of approximately 700 bp encoding the BglII/NotI-digested single-chain anti-hTfR antibody described above to construct a vector that could express in mammalian cells a fusion protein made of the single-chain anti-hTfR antibody fused on the N-terminal side of hI2S (hI2S-sc-anti-hTfR antibody fusion protein). *E. coli* (JP109) was transformed with the vector thus obtained, then disseminated on LB plates containing ampicillin (Amp), and cultured at 37° C. overnight. On the following day, each colony formed on the plates was cultured in LB medium, and the vector was collected from each colony. CHO cells were transformed with each of the collected vectors by electroporation, and subjected to a selection culture for one week, in the presence of neomycin, to give drug resistant cells expressing hI2S-sc-anti-hTfR antibody fusion protein for each clone.

The drug resistant cells obtained for each clone were cultured in a 1-L conical flask containing 200 mL of OptiCHO medium (Invitrogen, Inc.), and the culture supernatant was collected on the 7th day of culture. The collected culture supernatant was made free of particles through a 0.22 μm membrane filter, and applied to a HiTrap Q HP Sepharose column (column volume: 5 mL) that had been equilibrated with an equilibration buffer (20 mM HEPES, 100 mM NaCl, pH7.0). The column then was washed with a 5-fold column volume of the equilibration buffer, and hI2S-sc-anti-hTfR antibody fusion protein was eluted with a linear gradient using the equilibration buffer and an elution buffer (20 mM HEPES, 500 mM NaCl, pH6.0). Fractions that exhibited high enzyme activity of I2S was combined, concentrated approximately 10 folds using a 30 kDa cutoff ultrafiltration membrane concentration column, and stored at −80° C. In the above, hI2S enzyme activity was measured in accordance with the method described in WO 2012/101998.

[Test for Brain Distribution of hI2S-Sc-Anti-hTfR Antibody Fusion Protein on Mouse]

Male C57BL/6N mice were administered through the tail vein with the recombinant hI2S and the purified hI2S-sc-anti-hTfR antibody fusion protein obtained from each of the recombinant hI2S clones (M11, M23, M27, and B84), respectively, at the doses of 3 and 6 mg/kg (n=2/group). Seven hours after the administration, the mice were anesthetized with isoflurane, and after irrigating the mice through the vein with physiological saline, their brains were taken out. Each of the brains thus taken out was homogenized with T-PER Tissue Protein Extraction Reagent (Thermo Fisher Scientific K.K.) containing Protease Inhibitor Cocktail (Sigma-Aldrich Co. LLC.), and centrifuged, and the supernatant was collected. The supernatant thus collected was mixed with a biotinylated anti-hI2S monoclonal antibody and a sulfonated anti-hI2S monoclonal antibody, and allowed to react for one hour at room temperature to form a complex of the biotinylated anti-I2S monoclonal antibody, the hI2S-scrhTfR antibody fusion protein and the sulfonated anti-hI2S monoclonal antibody. The reaction mixture containing this complex then was added to Streptavidin Gold Plates (Meso Scale Diagnostics, LLC.) and allowed to react for one hour to let the complex bind to the plates via the binding between biotin and streptavidin. After the plates were washed, the concentration of the hI2S-scrhTfR fusion protein was determined by directing electric current through the plate using SECTOR Imager 6000 (Meso Scale Diagnostics, LLC.), thus applying an electrochemical stimulation to the sulfonation-labelled protein included in the complex, and measuring the intensity of fluorescence emitted from the sulfonation-labelled protein. In the above, the protein that was prepared in accordance with the method described in WO 2012/101998 was used as the recombinant hI2S.

[Assessment of Pharmacological Effect of hI2S-Sc-Anti-hTfR Antibody Fusion Protein on Hunter Syndrome Pathology Model Mouse]

Male iduronate 2-sulfatase gene knockout mice, model mice for the pathology of Hunter syndrome, were administered through the tail vein with the vehicle (physiological saline), the recombinant hI2S (rhI2S), or hI2S-sc-anti-hTfR antibody fusion protein at a dose of 3 mg/kg, once in three days, and three times in total (n=3/group). Three days after the final administration, the mice were anesthetized with isoflurane and euthanized with exsanguination, and the brain was taken out. The brain taken out was immediately subjected to rapid freezing in liquid nitrogen, and then lyophilized. The lyophilized brain was pulverized, and the thus pulverized brain tissue was suspended in 0.5 mol/L Tris-HCl buffer (pH 7.5), to which was added actinase E, and the mixture was left undisturbed for 16 hours at 60° C. to digest proteins. Then, the supernatant was collected after centrifugation, the concentration of glycosaminoglycans, i.e., the substrate for hI2S, contained in the supernatant was measured by Alcian Blue colorimetry using Wieslab sGAG quantitative kit (Euro-Diagnostica AB).

[Result 1: Test for Brain Distribution of hI2S-Sc-Anti-hTfR Antibody Fusion Protein on Mouse]

Figure 1B:
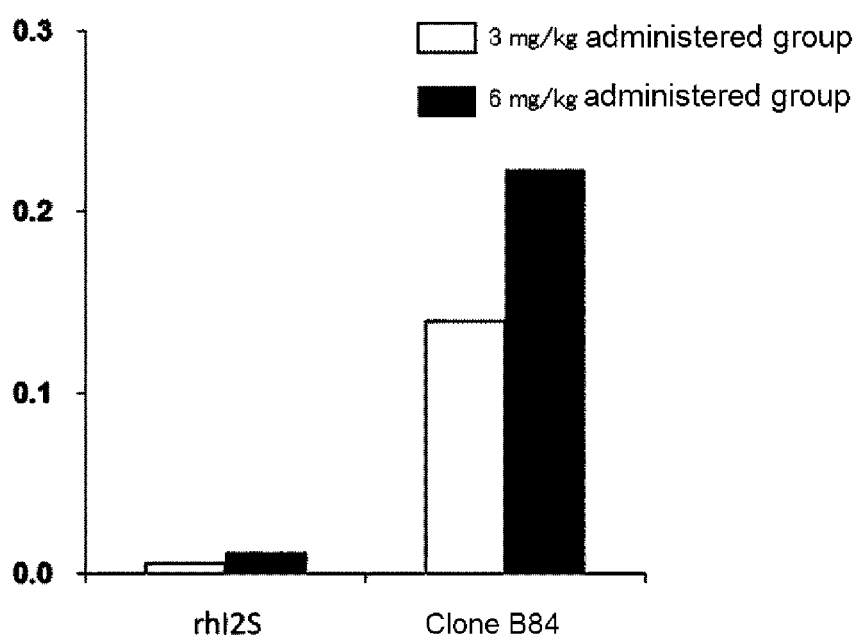
FIG. 1B illustrates the result of brain distribution test of hI2S-sc-anti-hTfR antibody fusion protein produced by transformed *E. coli* Clone M27, after it was injected into the tail vein of a mouse, along with the result with rhI2S. The vertical axis indicates the I2S concentration in brain homogenate (μg/wet weight)(mean of two animals per group).
Figure 1C:
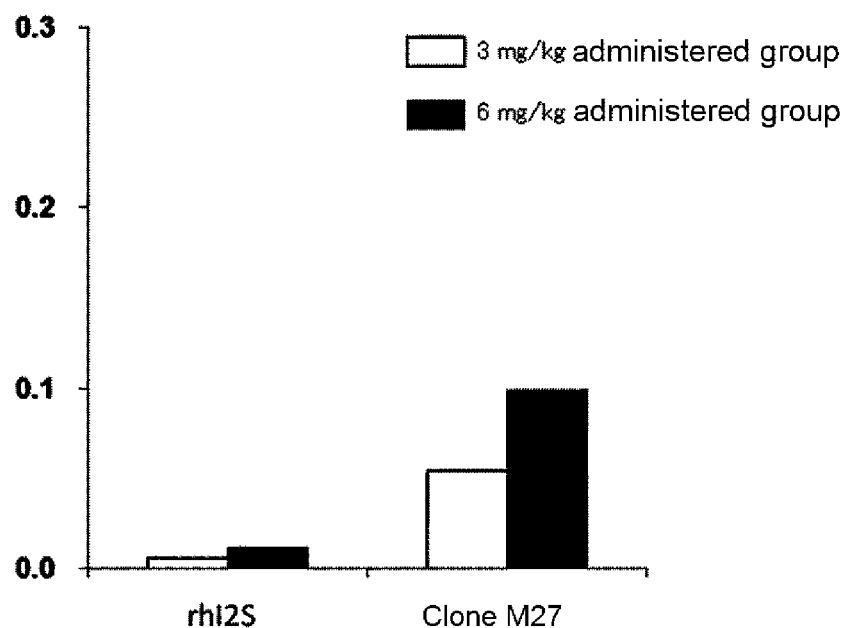
FIG. 1C illustrates the result of brain distribution test of hI2S-sc-anti-hTfR antibody fusion protein produced by transformed *E. coli* Clone B84, after it was injected into the tail vein of a mouse, along with the result with rhI2S. The vertical axis indicates the I2S concentration in brain homogenate (μg/wet weight)(mean of two animals per group).

The I2S concentration in the brain homogenate of the mice administered with rhI2S was below 0.01 μg/g wet weight in either of the 3 and 6 mg/kg-administered groups. On the other hand, in the mice administered with the hI2S-sc-anti-hTfR antibody fusion protein obtained from each clone, the I2S concentration in the brain homogenate was 10 to 20 times higher than the mice administered with rhI2S (FIG. 1A to FIG. 1C; Clone M23 not shown). Among the four clones, the I2S concentration in the brain homogenate was the highest with the mice administered with the hI2S-sc-anti-hTfR antibody fusion protein obtained from Clone B84 (FIG. 1B). The results indicate that the sc-anti-hTfR antibody obtained from the four clones have a function to efficiently transfer hI2S to the brain when they are fused with hI2S.

[Result 2: Assessment of Pharmacological Effect of hI2S-Sc-Anti-hTfR Antibody Fusion Protein on Hunter Syndrome Pathology Model Mouse]

Figure 2:
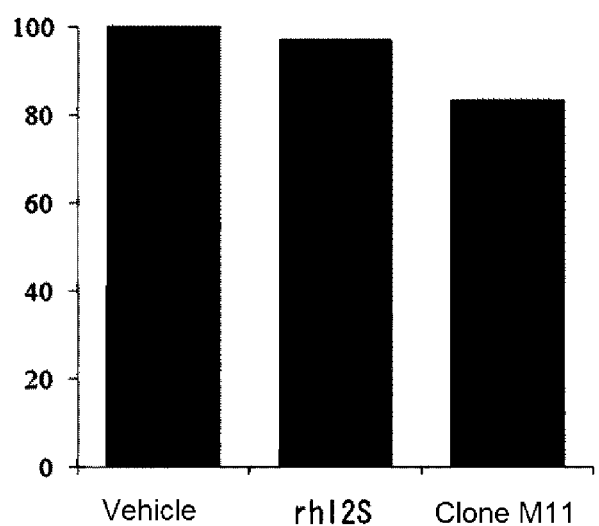
FIG. 2 illustrates the result of assessment of the pharmacological effect of hI2S-sc-anti-hTfR antibody fusion protein using model mice for the pathology of Hunter syndrome. The vertical axis indicates the amount of accumulated glycosaminoglycans (%) in the brain of mice administered with rhI2S and of the mice administered with hI2S-sc-anti-hTfR antibody fusion protein, in comparison with the amount of accumulated glycosaminoglycans, 100%, in the brain of mice administered with the vehicle (values, mean of three animals per group).

In the mice administered with recombinant hI2S, little decrease in the glycosaminoglycans accumulated in the brain was observed in comparison with the mice administered with the vehicle, whereas in the mice administered with hI2S-sc-anti-hTfR antibody fusion protein, the amount of glycosaminoglycans accumulated in the brain decreased to approximately 83% compared with the mice administered with the vehicle (FIG. 2). The results indicate that the hI2S-sc-anti-hTfR antibody fusion protein from Clone M11 can decompose glycosaminoglycans accumulated in the brain of the model mice for the pathology of Hunter syndrome. Therefore, when administered to a patient of Hunter syndrome, the hI2S-sc-anti-hTfR antibody fusion protein is capable of decomposing glycosaminoglycans accumulated in the brain of the patient, thus ameliorating central nervous system disorders in Hunter syndrome.

INDUSTRIAL APPLICABILITY

The present invention is useful in providing a protein that is brought into function in the central nervous system after administered into the blood, as it enables to provide a desired physiologically active protein in the form of a fusion protein with a single-chain anti-rhTfR antibody capable of transferring through the blood-brain barrier, and also as a protein that can function in the central nervous system after such transfer.

SEQUENCE LISTING

GP179-PCT_ST25

The invention claimed is:

1. A single-chain anti-human transferrin receptor antibody comprising an amino acid sequence selected from the group consisting of SEQ ID Nos: 4, 5, 6, and 7.

2. A DNA sequence encoding the antibody according to claim 1.

3. A fusion protein comprising the antibody according to claim 1 and another protein bound thereto on the C-terminal side.

4. The fusion protein according to claim 3 wherein the another protein is bound to the C-terminal side of the antibody by a linker sequence consisting of 3-50 amino acids.

5. The fusion protein according to claim 3, wherein said another protein is a lysosomal enzyme.

6. The fusion protein according to claim 5, wherein the lysosomal enzyme is human iduronate 2-sulfatase.

7. A DNA sequence encoding the fusion protein according to claim 3.

8. A mammalian expression vector comprising the DNA sequence according to claim 7.

9. A mammalian cell transformed with the mammalian expression vector according to claim 8.

10. The cell according to claim 9, wherein the mammalian cell is a CHO cell.

* * * * *

SEQUENCE LISTING

```
<160> NUMBER OF SEQ ID NOS: 61

<210> SEQ ID NO 1
<211> LENGTH: 15
<212> TYPE: PRT
<213> ORGANISM: Homo sapiens

<400> SEQUENCE: 1

Gly Lys Leu Val His Ala Asn Phe Gly Thr Lys Lys Asp Phe Glu
1               5                   10                  15
```

```
<210> SEQ ID NO 2
<211> LENGTH: 22
<212> TYPE: PRT
<213> ORGANISM: Homo sapiens

<400> SEQUENCE: 2

Ser Ser Gly Leu Pro Asn Ile Pro Val Gln Thr Ile Ser Arg Ala Ala
1               5                   10                  15

Ala Glu Lys Leu Phe Gly
            20

<210> SEQ ID NO 3
<211> LENGTH: 13
<212> TYPE: PRT
<213> ORGANISM: Homo sapiens

<400> SEQUENCE: 3

Val Gly Ala Thr Glu Trp Leu Glu Gly Tyr Leu Ser Ser
1               5                   10

<210> SEQ ID NO 4
<211> LENGTH: 248
<212> TYPE: PRT
<213> ORGANISM: Artificial Sequence
<220> FEATURE:
<223> OTHER INFORMATION: Clone M11

<400> SEQUENCE: 4

Asp Tyr Lys Asp Ile Val Met Thr Gln Ser His Lys Phe Met Ser Thr
1               5                   10                  15

Ser Val Gly Asp Arg Val Ser Ile Thr Cys Lys Ala Ser Gln Asp Val
            20                  25                  30

Gly Thr Ala Val Ala Trp Tyr Gln Gln Lys Pro Gly Gln Ser Pro Lys
        35                  40                  45

Leu Leu Ile Tyr Trp Ala Ser Thr Arg His Thr Gly Val Pro Asp Arg
    50                  55                  60

Phe Thr Gly Ser Gly Ser Gly Thr Asp Phe Thr Leu Thr Ile Ser Asn
65                  70                  75                  80

Val Gln Ser Glu Asp Leu Ala Asp Tyr Phe Cys Gln Gln Tyr Ser Ser
                85                  90                  95

Tyr Leu Thr Phe Gly Ala Gly Thr Lys Leu Glu Leu Lys Arg Gly Gly
            100                 105                 110

Gly Gly Ser Gly Gly Gly Gly Ser Gly Gly Gly Gly Ser Gly Gly Gly
        115                 120                 125

Gly Ser Glu Val Met Leu Val Glu Ser Gly Gly Asp Leu Val Lys Pro
    130                 135                 140

Gly Gly Ser Leu Lys Leu Ser Cys Ala Ala Ser Gly Phe Thr Phe Ser
145                 150                 155                 160

Ser Tyr Gly Met Ser Trp Val Arg Gln Thr Pro Asp Lys Arg Leu Glu
                165                 170                 175

Trp Val Ala Thr Ile Ser Ser Gly Gly Ser Tyr Thr Tyr Tyr Pro Asp
            180                 185                 190

Ser Val Lys Gly Arg Phe Thr Ile Ser Arg Asp Asn Ala Lys Asn Thr
        195                 200                 205

Leu Tyr Leu Gln Met Ser Ser Leu Lys Ser Glu Asp Thr Ala Met Tyr
    210                 215                 220

Tyr Cys Ala Leu Leu Arg Ser Asp Trp Tyr Phe Asp Val Trp Gly Ala
225                 230                 235                 240
```

```
Gly Thr Thr Val Thr Val Ser Ser
                245

<210> SEQ ID NO 5
<211> LENGTH: 245
<212> TYPE: PRT
<213> ORGANISM: Artificial Sequence
<220> FEATURE:
<223> OTHER INFORMATION: Clone M23

<400> SEQUENCE: 5

Asp Tyr Lys Asp Ile Val Ile Thr Gln Ser His Lys Phe Met Ser Thr
1               5                   10                  15

Ser Val Gly Asp Arg Val Ser Ile Thr Cys Lys Ala Ser Gln Asp Val
            20                  25                  30

Ser Thr Ala Val Ala Trp Tyr Gln Gln Lys Pro Gly Gln Ser Pro Lys
        35                  40                  45

Leu Leu Ile Tyr Ser Ala Ser Tyr Arg Tyr Thr Gly Val Pro Asp Arg
    50                  55                  60

Phe Thr Gly Ser Gly Ser Gly Thr Asp Phe Thr Phe Thr Ile Ser Ser
65                  70                  75                  80

Val Gln Ala Glu Asp Leu Ala Val Tyr Tyr Cys Gln Gln His Tyr Ser
                85                  90                  95

Thr Pro Tyr Thr Phe Gly Gly Gly Thr Lys Leu Glu Ile Lys Arg Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Gln Ser Gly Ala Glu Leu Val Arg
    130                 135                 140

Pro Gly Ala Ser Val Thr Leu Ser Cys Lys Ala Ser Gly Tyr Thr Phe
145                 150                 155                 160

Thr Asp Tyr Glu Met His Trp Val Lys Gln Thr Pro Val His Gly Leu
                165                 170                 175

Glu Trp Ile Gly Ala Ile Asp Pro Glu Thr Gly Gly Thr Ala Tyr Asn
            180                 185                 190

Gln Lys Phe Lys Gly Lys Ala Thr Leu Thr Ala Asp Lys Ser Ser Ser
        195                 200                 205

Thr Ala Tyr Met Glu Leu Arg Ser Leu Thr Ser Glu Asp Ser Ala Val
    210                 215                 220

Tyr Tyr Cys Thr Gly Trp Gly Phe Asp Tyr Trp Gly Gln Gly Thr Thr
225                 230                 235                 240

Leu Thr Val Ser Ser
                245

<210> SEQ ID NO 6
<211> LENGTH: 247
<212> TYPE: PRT
<213> ORGANISM: Artificial Sequence
<220> FEATURE:
<223> OTHER INFORMATION: Clone M27

<400> SEQUENCE: 6

Asp Tyr Lys Asp Ile Val Met Thr Gln Ser His Lys Phe Met Ser Thr
1               5                   10                  15

Ser Val Gly Asp Arg Val Ser Ile Thr Cys Lys Ala Ser Gln Asp Val
            20                  25                  30

Gly Thr Ala Val Ala Trp Tyr Gln Gln Lys Pro Gly Ser Pro Lys
        35                  40                  45
```

```
Leu Leu Ile Tyr Trp Ala Ser Thr Arg His Thr Gly Val Pro Asp Arg
         50                  55                  60

Phe Thr Gly Ser Gly Ser Gly Thr Asp Phe Thr Leu Thr Ile Ser Asn
 65                  70                  75                  80

Val Gln Ser Glu Asp Leu Ala Asp Tyr Phe Cys Gln Gln Tyr Ser Ser
                 85                  90                  95

Tyr Pro Tyr Thr Phe Gly Gly Gly Thr Lys Leu Glu Ile Lys Arg Gly
                100                 105                 110

Gly Gly Gly Ser Gly Gly Gly Ser Gly Gly Gly Ser Gly Gly
             115                 120                 125

Gly Gly Ser Gln Val Gln Leu Gln Gln Pro Gly Ser Glu Leu Val Arg
        130                 135                 140

Pro Gly Ala Ser Val Lys Leu Ser Cys Lys Ala Ser Gly Tyr Thr Phe
145                 150                 155                 160

Thr Ser Tyr Trp Met His Trp Val Lys Gln Arg Pro Gly Gln Gly Leu
                165                 170                 175

Glu Trp Ile Gly Asn Ile Tyr Pro Gly Ser Gly Ser Thr Asn Tyr Asp
                180                 185                 190

Glu Lys Phe Lys Ser Lys Ala Thr Leu Thr Val Asp Thr Ser Ser Ser
            195                 200                 205

Thr Ala Tyr Met Gln Leu Ser Ser Leu Thr Ser Glu Asp Ser Ala Val
        210                 215                 220

Tyr Tyr Cys Thr Arg Gly Ala Thr Ala Leu Asp Tyr Trp Gly Gln Gly
225                 230                 235                 240

Thr Thr Leu Thr Val Ser Ser
                245

<210> SEQ ID NO 7
<211> LENGTH: 131
<212> TYPE: PRT
<213> ORGANISM: Artificial Sequence
<220> FEATURE:
<223> OTHER INFORMATION: Clone B84

<400> SEQUENCE: 7

Gln Val Gln Leu Gln Glu Ser Gly Pro Gly Leu Val Lys Pro Ser Glu
 1               5                  10                  15

Thr Leu Ser Leu Thr Cys Thr Val Ser Ala Gly Ser Ile Ser Ser Thr
                20                  25                  30

Ser Thr Ser Tyr Tyr Trp Gly Trp Ile Arg Gln Ser Pro Gly Lys Gly
            35                  40                  45

Leu Glu Trp Ile Gly Ser Ile Tyr Tyr Ser Gly Arg Thr Tyr Tyr Asn
 50                  55                  60

Pro Ser Leu Lys Ser Arg Val Thr Ile Ser Val Asp Arg Pro Asn Asn
 65                  70                  75                  80

Gln Phe Ser Leu Lys Val Ser Ser Val Thr Ala Ala Asp Ser Ala Val
                85                  90                  95

Tyr Tyr Cys Ala Arg His Arg Arg Val Leu Leu Trp Ile Gly Glu Leu
            100                 105                 110

Leu Asp Asp Tyr Asp Arg Asp Val Trp Gly Gln Gly Thr Met Val Thr
        115                 120                 125

Val Ser Ser
    130

<210> SEQ ID NO 8
```

```
<211> LENGTH: 15
<212> TYPE: PRT
<213> ORGANISM: Artificial Sequence
<220> FEATURE:
<223> OTHER INFORMATION: Linker 1

<400> SEQUENCE: 8

Gly Gly Gly Gly Ser Gly Gly Gly Gly Ser Gly Gly Gly Gly Ser
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Linker 2

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 38
<212> TYPE: DNA
<213> ORGANISM: Artificial Sequence
<220> FEATURE:
<223> OTHER INFORMATION: VL-FW1, synthetic sequence

<400> SEQUENCE: 10
ttcatggcgg actacaaaga yatccagctg actcagcc                              38

<210> SEQ ID NO 11
<211> LENGTH: 38
<212> TYPE: DNA
<213> ORGANISM: Artificial Sequence
<220> FEATURE:
<223> OTHER INFORMATION: VL-FW2, synthetic sequence

<400> SEQUENCE: 11
ttcatggcgg actacaaaga yattgttctc wcccagtc                              38

<210> SEQ ID NO 12
<211> LENGTH: 38
<212> TYPE: DNA
<213> ORGANISM: Artificial Sequence
<220> FEATURE:
<223> OTHER INFORMATION: VL-FW3, synthetic sequence

<400> SEQUENCE: 12
ttcatggcgg actacaaaga yattgtgmtm actcagtc                              38

<210> SEQ ID NO 13
<211> LENGTH: 38
<212> TYPE: DNA
<213> ORGANISM: Artificial Sequence
<220> FEATURE:
<223> OTHER INFORMATION: VL-FW4, synthetic sequence

<400> SEQUENCE: 13
ttcatggcgg actacaaaga yattgtgytr acacagtc                              38

<210> SEQ ID NO 14
<211> LENGTH: 38
<212> TYPE: DNA
<213> ORGANISM: Artificial Sequence
<220> FEATURE:
<223> OTHER INFORMATION: VL-FW5, synthetic sequence
```

<400> SEQUENCE: 14
ttcatggcgg actacaaaga yattgtratg acmcagtc                                38

<210> SEQ ID NO 15
<211> LENGTH: 38
<212> TYPE: DNA
<213> ORGANISM: Artificial Sequence
<220> FEATURE:
<223> OTHER INFORMATION: VL-FW6, synthetic sequence

<400> SEQUENCE: 15
ttcatggcgg actacaaaga yattmagatr amccagtc                                38

<210> SEQ ID NO 16
<211> LENGTH: 38
<212> TYPE: DNA
<213> ORGANISM: Artificial Sequence
<220> FEATURE:
<223> OTHER INFORMATION: VL-FW7, synthetic sequence

<400> SEQUENCE: 16
ttcatggcgg actacaaaga yattcagatg aydcagtc                                38

<210> SEQ ID NO 17
<211> LENGTH: 38
<212> TYPE: DNA
<213> ORGANISM: Artificial Sequence
<220> FEATURE:
<223> OTHER INFORMATION: VL-FW8, synthetic sequence

<400> SEQUENCE: 17
ttcatggcgg actacaaaga yatycagatg acacagac                                38

<210> SEQ ID NO 18
<211> LENGTH: 38
<212> TYPE: DNA
<213> ORGANISM: Artificial Sequence
<220> FEATURE:
<223> OTHER INFORMATION: VL-FW9, synthetic sequence

<400> SEQUENCE: 18
ttcatggcgg actacaaaga yattgttctc awccagtc                                38

<210> SEQ ID NO 19
<211> LENGTH: 38
<212> TYPE: DNA
<213> ORGANISM: Artificial Sequence
<220> FEATURE:
<223> OTHER INFORMATION: VL-FW10, synthetic sequence

<400> SEQUENCE: 19
ttcatggcgg actacaaaga yattgwgcts acccaatc                                38

<210> SEQ ID NO 20
<211> LENGTH: 38
<212> TYPE: DNA
<213> ORGANISM: Artificial Sequence
<220> FEATURE:
<223> OTHER INFORMATION: VL-FW11, synthetic sequence

<400> SEQUENCE: 20
ttcatggcgg actacaaaga yattstratg acccartc                                38

<210> SEQ ID NO 21

```
<210> SEQ ID NO 21
<211> LENGTH: 38
<212> TYPE: DNA
<213> ORGANISM: Artificial Sequence
<220> FEATURE:
<223> OTHER INFORMATION: VL-FW12, synthetic sequence

<400> SEQUENCE: 21
ttcatggcgg actacaaaga yrttktgatg acccarac                              38

<210> SEQ ID NO 22
<211> LENGTH: 38
<212> TYPE: DNA
<213> ORGANISM: Artificial Sequence
<220> FEATURE:
<223> OTHER INFORMATION: VL-FW13, synthetic sequence

<400> SEQUENCE: 22
ttcatggcgg actacaaaga yattgtgatg acbcagkc                              38

<210> SEQ ID NO 23
<211> LENGTH: 38
<212> TYPE: DNA
<213> ORGANISM: Artificial Sequence
<220> FEATURE:
<223> OTHER INFORMATION: VL-FW14, synthetic sequence

<400> SEQUENCE: 23
ttcatggcgg actacaaaga yattgtgata acycagga                              38

<210> SEQ ID NO 24
<211> LENGTH: 38
<212> TYPE: DNA
<213> ORGANISM: Artificial Sequence
<220> FEATURE:
<223> OTHER INFORMATION: VL-FW15, synthetic sequence

<400> SEQUENCE: 24
ttcatggcgg actacaaaga yattgtgatg acccagwt                              38

<210> SEQ ID NO 25
<211> LENGTH: 38
<212> TYPE: DNA
<213> ORGANISM: Artificial Sequence
<220> FEATURE:
<223> OTHER INFORMATION: VL-FW16, synthetic sequence

<400> SEQUENCE: 25
ttcatggcgg actacaaaga yattgtgatg acacaacc                              38

<210> SEQ ID NO 26
<211> LENGTH: 38
<212> TYPE: DNA
<213> ORGANISM: Artificial Sequence
<220> FEATURE:
<223> OTHER INFORMATION: VL-FW17, synthetic sequence

<400> SEQUENCE: 26
ttcatggcgg actacaaaga yattttgctg actcagtc                              38

<210> SEQ ID NO 27
<211> LENGTH: 40
<212> TYPE: DNA
<213> ORGANISM: Artificial Sequence
<220> FEATURE:
<223> OTHER INFORMATION: VL-FW18, synthetic sequence

<400> SEQUENCE: 27
```
ttcatggcgg actacaaaga tgctgttgta ctcaggaatc                    40

<210> SEQ ID NO 28
<211> LENGTH: 65
<212> TYPE: DNA
<213> ORGANISM: Artificial Sequence
<220> FEATURE:
<223> OTHER INFORMATION: VL-RV1, synthetic sequence

<400> SEQUENCE: 28
ggagccgccg ccgccagaac caccaccacc agaaccacca ccaccacgtt tgatttccag    60
cttgg                                                              65

<210> SEQ ID NO 29
<211> LENGTH: 65
<212> TYPE: DNA
<213> ORGANISM: Artificial Sequence
<220> FEATURE:
<223> OTHER INFORMATION: VL-RV2, synthetic sequence

<400> SEQUENCE: 29
ggagccgccg ccgccagaac caccaccacc agaaccacca ccaccacgtt ttatttccag    60
cttgg                                                              65

<210> SEQ ID NO 30
<211> LENGTH: 65
<212> TYPE: DNA
<213> ORGANISM: Artificial Sequence
<220> FEATURE:
<223> OTHER INFORMATION: VL-RV3, synthetic sequence

<400> SEQUENCE: 30
ggagccgccg ccgccagaac caccaccacc agaaccacca ccaccacgtt ttatttccaa    60
ctttg                                                              65

<210> SEQ ID NO 31
<211> LENGTH: 65
<212> TYPE: DNA
<213> ORGANISM: Artificial Sequence
<220> FEATURE:
<223> OTHER INFORMATION: VL-RV4, synthetic sequence

<400> SEQUENCE: 31
ggagccgccg ccgccagaac caccaccacc agaaccacca ccaccacgtt tcagctccag    60
cttgg                                                              65

<210> SEQ ID NO 32
<211> LENGTH: 65
<212> TYPE: DNA
<213> ORGANISM: Artificial Sequence
<220> FEATURE:
<223> OTHER INFORMATION: VL-RV5, synthetic sequence

<400> SEQUENCE: 32
ggagccgccg ccgccagaac caccaccacc agaaccacca ccaccacta ggacagtcag     60 tttgg                                                              65

<210> SEQ ID NO 33
<211> LENGTH: 50
<212> TYPE: DNA
<213> ORGANISM: Artificial Sequence
<220> FEATURE:

<223> OTHER INFORMATION: VH-FW1, synthetic sequence

<400> SEQUENCE: 33
ggcggcggcg gctccggtgg tggtggatcc gakgtrmagc ttcaggagtc          50

<210> SEQ ID NO 34
<211> LENGTH: 50
<212> TYPE: DNA
<213> ORGANISM: Artificial Sequence
<220> FEATURE:
<223> OTHER INFORMATION: VH-FW2, synthetic sequence

<400> SEQUENCE: 34
ggcggcggcg gctccggtgg tggtggatcc gaggtbcagc tbcagcagtc          50

<210> SEQ ID NO 35
<211> LENGTH: 50
<212> TYPE: DNA
<213> ORGANISM: Artificial Sequence
<220> FEATURE:
<223> OTHER INFORMATION: VH-FW3, synthetic sequence

<400> SEQUENCE: 35
ggcggcggcg gctccggtgg tggtggatcc caggtgcagc tgaagsastc          50

<210> SEQ ID NO 36
<211> LENGTH: 50
<212> TYPE: DNA
<213> ORGANISM: Artificial Sequence
<220> FEATURE:
<223> OTHER INFORMATION: VH-FW4, synthetic sequence

<400> SEQUENCE: 36
ggcggcggcg gctccggtgg tggtggatcc gaggtccarc tgcaacartc          50

<210> SEQ ID NO 37
<211> LENGTH: 50
<212> TYPE: DNA
<213> ORGANISM: Artificial Sequence
<220> FEATURE:
<223> OTHER INFORMATION: VH-FW5, synthetic sequence

<400> SEQUENCE: 37
ggcggcggcg gctccggtgg tggtggatcc caggtycagc tbcagcartc          50

<210> SEQ ID NO 38
<211> LENGTH: 50
<212> TYPE: DNA
<213> ORGANISM: Artificial Sequence
<220> FEATURE:
<223> OTHER INFORMATION: VH-FW6, synthetic sequence

<400> SEQUENCE: 38
ggcggcggcg gctccggtgg tggtggatcc caggtycarc tgcagcagtc          50

<210> SEQ ID NO 39
<211> LENGTH: 50
<212> TYPE: DNA
<213> ORGANISM: Artificial Sequence
<220> FEATURE:
<223> OTHER INFORMATION: VH-FW7, synthetic sequence

<400> SEQUENCE: 39
ggcggcggcg gctccggtgg tggtggatcc caggtccacg tgaagcagtc          50

```
<210> SEQ ID NO 40
<211> LENGTH: 50
<212> TYPE: DNA
<213> ORGANISM: Artificial Sequence
<220> FEATURE:
<223> OTHER INFORMATION: VH-FW8, synthetic sequence

<400> SEQUENCE: 40
ggcggcggcg gctccggtgg tgtggatcc gaggtgaass tggtggaatc          50

<210> SEQ ID NO 41
<211> LENGTH: 50
<212> TYPE: DNA
<213> ORGANISM: Artificial Sequence
<220> FEATURE:
<223> OTHER INFORMATION: VH-FW9, synthetic sequence

<400> SEQUENCE: 41
ggcggcggcg gctccggtgg tgtggatcc gavgtgawgy tggtggagtc          50

<210> SEQ ID NO 42
<211> LENGTH: 50
<212> TYPE: DNA
<213> ORGANISM: Artificial Sequence
<220> FEATURE:
<223> OTHER INFORMATION: VH-FW10, synthetic sequence

<400> SEQUENCE: 42
ggcggcggcg gctccggtgg tgtggatcc gaggtgcags kggtggagtc          50

<210> SEQ ID NO 43
<211> LENGTH: 50
<212> TYPE: DNA
<213> ORGANISM: Artificial Sequence
<220> FEATURE:
<223> OTHER INFORMATION: VH-FW11, synthetic sequence

<400> SEQUENCE: 43
ggcggcggcg gctccggtgg tgtggatcc gakgtgcamc tggtggagtc          50

<210> SEQ ID NO 44
<211> LENGTH: 50
<212> TYPE: DNA
<213> ORGANISM: Artificial Sequence
<220> FEATURE:
<223> OTHER INFORMATION: VH-FW12, synthetic sequence

<400> SEQUENCE: 44
ggcggcggcg gctccggtgg tgtggatcc gaggtgaagc tgatggartc          50

<210> SEQ ID NO 45
<211> LENGTH: 50
<212> TYPE: DNA
<213> ORGANISM: Artificial Sequence
<220> FEATURE:
<223> OTHER INFORMATION: VH-FW13, synthetic sequence

<400> SEQUENCE: 45
ggcggcggcg gctccggtgg tgtggatcc gaggtgcarc ttgttgagtc          50

<210> SEQ ID NO 46
<211> LENGTH: 50
<212> TYPE: DNA
<213> ORGANISM: Artificial Sequence
<220> FEATURE:
<223> OTHER INFORMATION: VH-FW14, synthetic sequence
```

```
<400> SEQUENCE: 46
ggcggcggcg gctccggtgg tgtgggatcc gargtraagc ttctcgagtc        50

<210> SEQ ID NO 47
<211> LENGTH: 50
<212> TYPE: DNA
<213> ORGANISM: Artificial Sequence
<220> FEATURE:
<223> OTHER INFORMATION: VH-FW15, synthetic sequence

<400> SEQUENCE: 47
ggcggcggcg gctccggtgg tgtgggatcc gaagtgaars ttgaggagtc        50

<210> SEQ ID NO 48
<211> LENGTH: 52
<212> TYPE: DNA
<213> ORGANISM: Artificial Sequence
<220> FEATURE:
<223> OTHER INFORMATION: VH-FW16, synthetic sequence

<400> SEQUENCE: 48
ggcggcggcg gctccggtgg tgtgggatcc caggttactc traaagwgts tg     52

<210> SEQ ID NO 49
<211> LENGTH: 50
<212> TYPE: DNA
<213> ORGANISM: Artificial Sequence
<220> FEATURE:
<223> OTHER INFORMATION: VH-FW17, synthetic sequence

<400> SEQUENCE: 49
ggcggcggcg gctccggtgg tgtgggatcc caggtccaac tvcagcarcc        50

<210> SEQ ID NO 50
<211> LENGTH: 50
<212> TYPE: DNA
<213> ORGANISM: Artificial Sequence
<220> FEATURE:
<223> OTHER INFORMATION: VH-FW18, synthetic sequence

<400> SEQUENCE: 50
ggcggcggcg gctccggtgg tgtgggatcc gatgtgaact tggaagtgtc        50

<210> SEQ ID NO 51
<211> LENGTH: 50
<212> TYPE: DNA
<213> ORGANISM: Artificial Sequence
<220> FEATURE:
<223> OTHER INFORMATION: VH-FW19, synthetic sequence

<400> SEQUENCE: 51
ggcggcggcg gctccggtgg tgtgggatcc gaggtgaagg tcatcgagtc        50

<210> SEQ ID NO 52
<211> LENGTH: 39
<212> TYPE: DNA
<213> ORGANISM: Artificial Sequence
<220> FEATURE:
<223> OTHER INFORMATION: VH-RV1, synthetic sequence

<400> SEQUENCE: 52
ggcaagcttt acctgcagcg aggaaacggt gaccgtggt                    39

<210> SEQ ID NO 53
<211> LENGTH: 39
```

```
<212> TYPE: DNA
<213> ORGANISM: Artificial Sequence
<220> FEATURE:
<223> OTHER INFORMATION: VH-RV2, synthetic sequence

<400> SEQUENCE: 53
ggcaagcttt acctgcagcg aggagactgt gagagtggt                              39

<210> SEQ ID NO 54
<211> LENGTH: 39
<212> TYPE: DNA
<213> ORGANISM: Artificial Sequence
<220> FEATURE:
<223> OTHER INFORMATION: VH-RV3, synthetic sequence

<400> SEQUENCE: 54
ggcaagcttt acctgcagcg cagagacagt gaccagagt                              39

<210> SEQ ID NO 55
<211> LENGTH: 39
<212> TYPE: DNA
<213> ORGANISM: Artificial Sequence
<220> FEATURE:
<223> OTHER INFORMATION: VH-RV4, synthetic sequence

<400> SEQUENCE: 55
ggcaagcttt acctgcagcg aggagacggt gactgaggt                              39

<210> SEQ ID NO 56
<211> LENGTH: 25
<212> TYPE: DNA
<213> ORGANISM: Artificial Sequence
<220> FEATURE:
<223> OTHER INFORMATION: Second-FW, synthetic sequence

<400> SEQUENCE: 56
ggcgaattca tggcggacta caaag                                             25

<210> SEQ ID NO 57
<211> LENGTH: 19
<212> TYPE: DNA
<213> ORGANISM: Artificial Sequence
<220> FEATURE:
<223> OTHER INFORMATION: Second-RV, synthetic sequence

<400> SEQUENCE: 57
ggcaagcttt actgcagcg                                                    19

<210> SEQ ID NO 58
<211> LENGTH: 20
<212> TYPE: DNA
<213> ORGANISM: Artificial Sequence
<220> FEATURE:
<223> OTHER INFORMATION: I2S-f, synthetic sequence

<400> SEQUENCE: 58
acgcctattg ctgcaggatg                                                   20

<210> SEQ ID NO 59
<211> LENGTH: 20
<212> TYPE: DNA
<213> ORGANISM: Artificial Sequence
<220> FEATURE:
<223> OTHER INFORMATION: I2S-r, synthetic sequence

<400> SEQUENCE: 59
```

```
aaacgaccag ctctaactcc                                                     20

<210> SEQ ID NO 60
<211> LENGTH: 30
<212> TYPE: DNA
<213> ORGANISM: Artificial Sequence
<220> FEATURE:
<223> OTHER INFORMATION: I2S-f2, synthetic sequence

<400> SEQUENCE: 60
atactcgagg ccaccatgcc gccaccccgg                                          30

<210> SEQ ID NO 61
<211> LENGTH: 30
<212> TYPE: DNA
<213> ORGANISM: Artificial Sequence
<220> FEATURE:
<223> OTHER INFORMATION: I2S-r2, synthetic sequence

<400> SEQUENCE: 61
ttcttatgcg gccgctcaag gcatcaacaa                                          30
```